US00PP36026P2

(12) United States Plant Patent
Aguilar Morán

(10) Patent No.: US PP36,026 P2
(45) Date of Patent: Jul. 23, 2024

(54) DESSERT BANANA PLANT NAMED "NW02"

(50) Latin Name: *M. acuminata*
Varietal Denomination: NW02

(71) Applicant: Fundación Hondureña de Investigación Agrícola (FHIA), San Pedro Sula (HN)

(72) Inventor: Juan Fernando Aguilar Morán, La Lima (HN)

(73) Assignee: Fundación Hondureña de Investigación Agrícola (FHIA) (HN)

( * ) Notice: Subject to any disclaimer, the term of this patent is extended or adjusted under 35 U.S.C. 154(b) by 0 days.

(21) Appl. No.: 18/469,776

(22) Filed: Sep. 19, 2023

(51) Int. Cl.
*A01H 5/08* (2018.01)

(52) U.S. Cl.
USPC ..... Plt./160

(58) Field of Classification Search
USPC ..... Plt./160
CPC ..... A01H 6/00; A01H 5/08
See application file for complete search history.

*Primary Examiner* — Keith O. Robinson
(74) *Attorney, Agent, or Firm* — Garvey, Smith & Nehrbass, Patent Attorneys, L.L.C.; Seth M. Nehrbass; Fabian M. Nehrbass

(57) ABSTRACT

'NW02' is a hybrid dessert banana variety with a dwarf stature and produces small bunches with high-quality fruit.

6 Drawing Sheets

Latin name of the genus and species of the plant claimed: This tetraploid plant has only *M. acuminata* in its pedigree. This tetraploid hybrid is a product of an inter-specific cross between two triploid (AAA) cultivars. Its Latin name is *M. acuminata* representing four genomes (AAAA) of this genus and species.

Variety denomination: 'NW02'.

STATEMENT REGARDING FEDERALLY SPONSORED RESEARCH OR DEVELOPMENT

Not applicable.

BACKGROUND OF THE INVENTION

1. Field of the Invention

This invention relates to a new and distinctive hybrid banana variety named 'NW02'. This new hybrid variety was the result of a field cross performed in 2016 in La Lima Cortés, Honduras, between 'Novak' used as a female and 'Williams' used as a male (Both unpatented). 'Novak' is a medium-sized triploid plant (AAA) cavendish type. 'Williams' is a medium to tall plant and is a cultivar of the Giant Cavendish type in the Cavendish Subgroup. It is one of the most widely grown cultivars in commercial plantations. Both parents are resistant to *Fusarium oxysporum* races one but susceptible to Race 4; furthermore, they are susceptible to the Black Sigatoka leaf spot (*Mycosphaerella fijiensis*).

Both parents were selected from a germplasm collection and are among the most traded bananas worldwide. 'NW02' is a Cavendish tetraploid (AAAA) created especially for the genetic improvement of the Cavendish group.

'NW02' was selected in 2018 from several first-generation seedlings from the cross between 'Novak' and 'Williams'. It was chosen as a tetraploid hybrid different from the "Cavendish type" stature but maintaining the taste of its parental lines and producing bunches of 12 kilograms with fruits shaped differently from their Cavendish parents.

'NW02' was asexually reproduced by corms by the breeder in La Lima Cortes, Honduras. All plants and fruit run true to the initially selected plant and are identical in all aspects.

The fruits of the 'NW02' variety have a flavor that is like that of its parent plants, 'Novak', and 'Williams'. The leaves of 'NW02' also share the same shape, and the pseudostem has the same color as its parents. However, there are noticeable differences between them. For instance, 'NW02' is a short plant, unlike 'Novak' and 'Williams', which are medium-sized plants. Additionally, the bunch size and finger shape of the 'NW02' variety are smaller when compared to its parents. It's important to note that these comparisons are made with reference to a standard variety, as one of the relatives of 'NW02' ('Williams') is the world's most produced and marketed commercial variety.

BRIEF SUMMARY OF THE INVENTION

'NW02' is a hybrid dessert banana variety with a dwarf stature and produces small bunches with high-quality fruit.

BRIEF DESCRIPTION OF THE PHOTOGRAPHS

The figures describe the characteristics of the 'NW02' hybrid banana variety. The color shown in the photographs is as nearly accurate as reasonably possible in this type's color representation.

FIG. 1 shows the typical appearance of a plant at ten (10) months old;

FIG. 2A-B shows blotches at the petiole base (A) and a petiole canal leaf (B);

FIG. 3A-C shows the shape of a leaf blade base (A) and leaf upper (B) and lower (C) surfaces;

FIG. 4 shows typical suckers;

Figure 1:
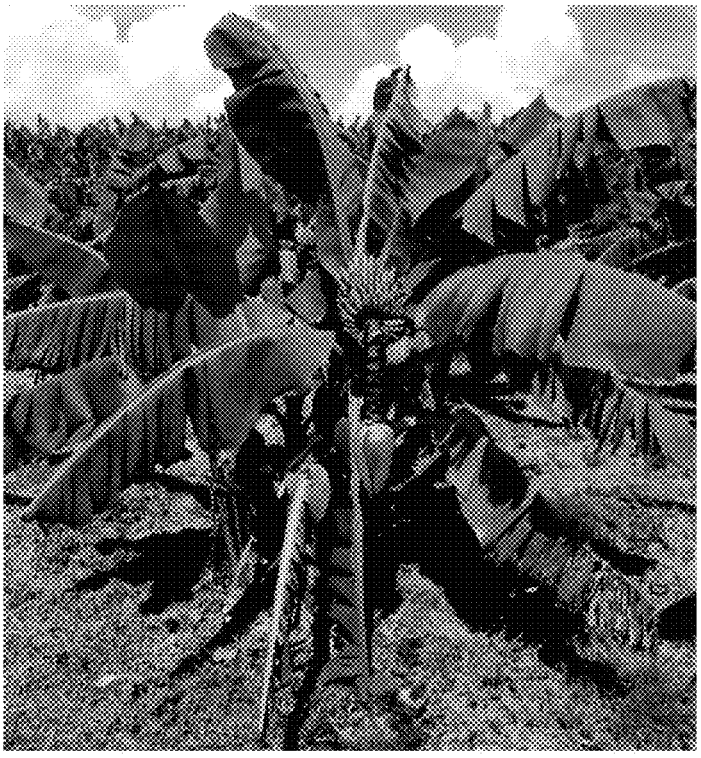
Figures 2A, 2B:
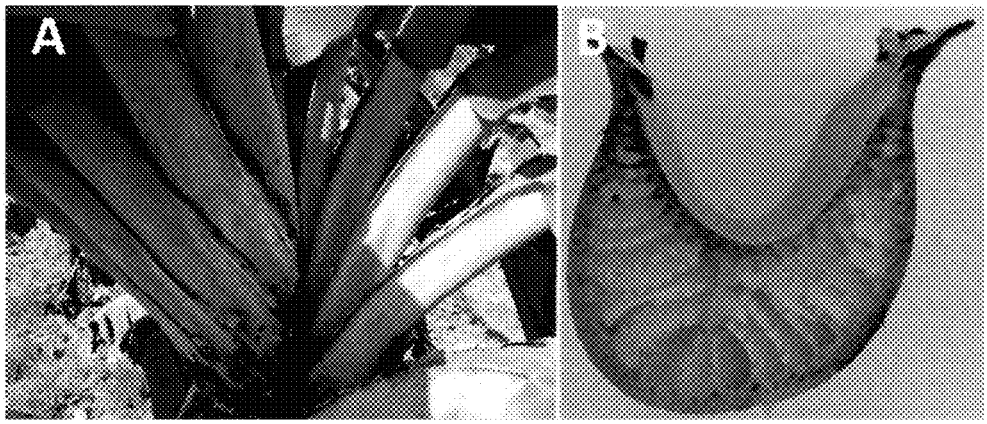
Figure 5:
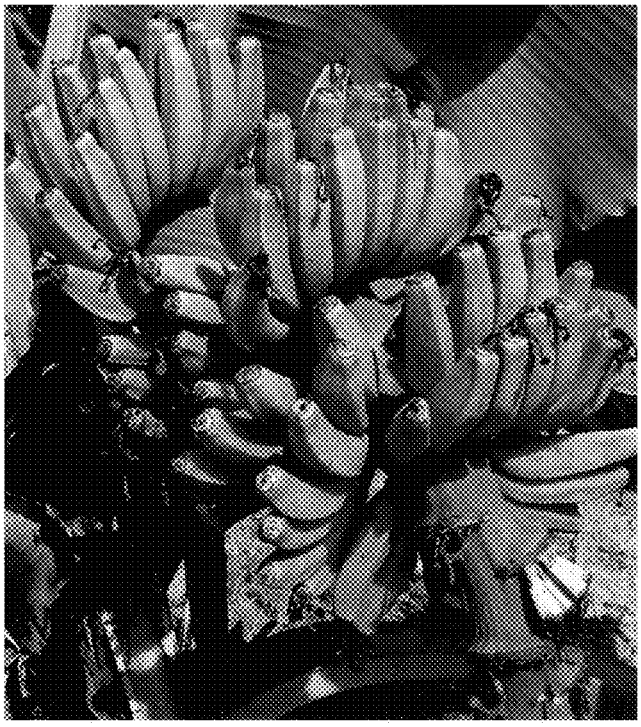
FIG. 5 shows a typical fruit bunch.
Figure 6:
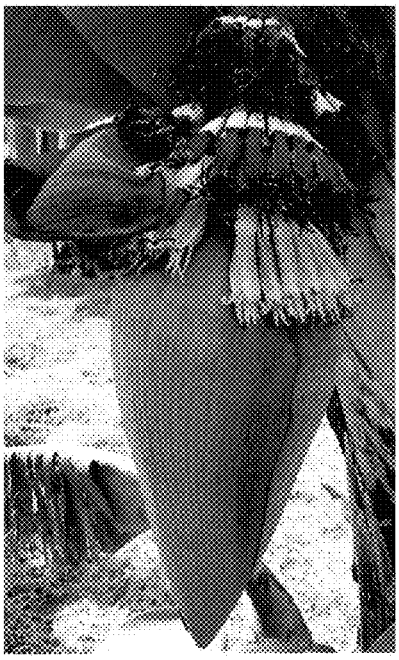
FIG. 6 shows a male bud.
Figures 9A, 9B:
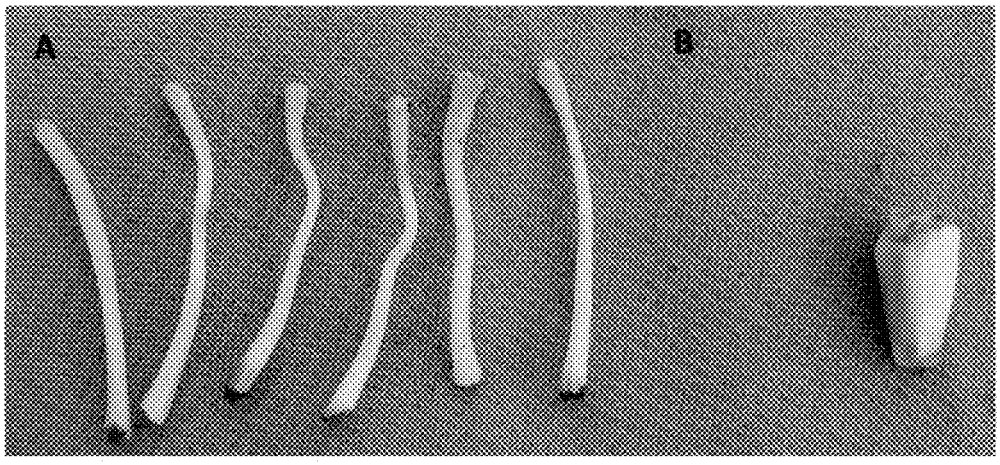
Figure 10:
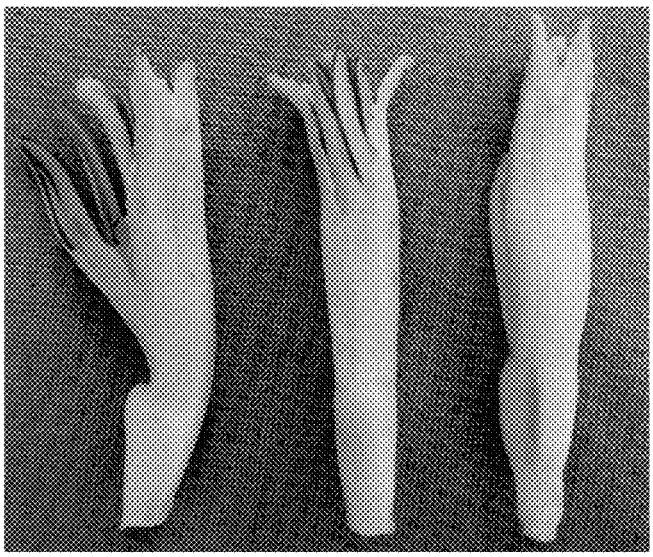
Figure 11:
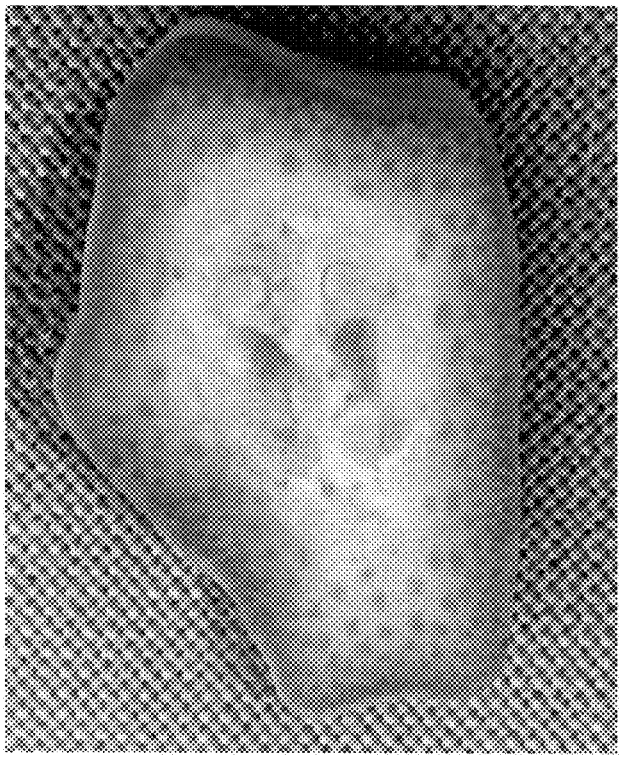
Figure 12:
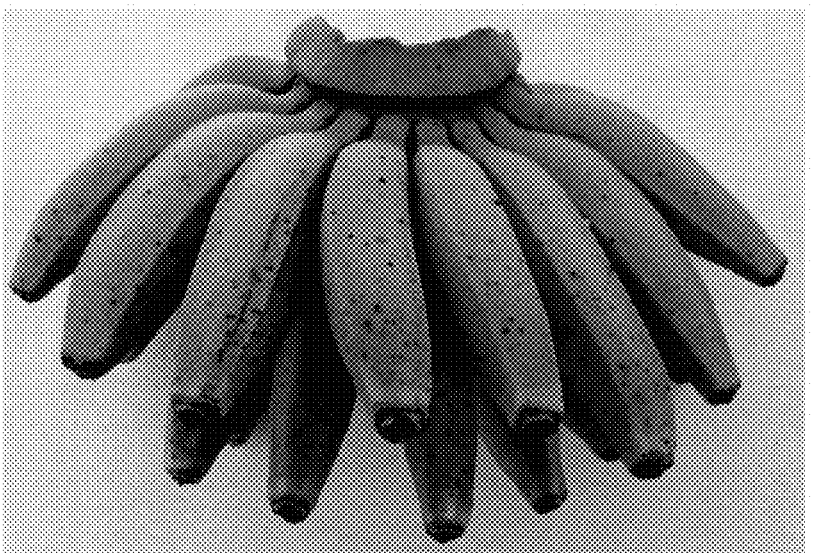

FIG. 7A-C shows bracts of a male bud;

FIG. 8A-D shows free tepal (A) and compound tepals (B-D) lobes;

FIG. 9A-B shows style shape (A) and ovary (B);
FIG. 10 shows a typical male flower;
FIG. 11 shows rowed ovules; and
FIG. 12 shows a typical second hand.

DETAILED BOTANICAL DESCRIPTION

The following is a detailed botanical description of the new variety 'NW02'. The report is from plants located in La Lima, Cortés, Honduras, evaluated in 2023. The descriptions concord with the internationally standardized "Descriptors for Banana (*Musa* spp.)" elaborated by IPGRI/INIBAP/CIRAD, 1996, and the U.K.'s Royal Horticultural Society's Color Chart, 2001. The 'NW02' plant and its fruit may vary slightly from the detailed descriptors shown below due to cultural practices, soil types, and climatic conditions under which the variety may be cultivated.

| | |
|---|---|
| Leaf habit | Intermediate |
| Dwarfism | Dwarf type |
| Pseudostem length | 1.07 meters |
| Pseudostem diameter | 0.47 meters |
| Pseudostem height | 1.5 to 2 meters |
| Pseudostem aspect | Normal |
| Pseudostem color | Green (146D, RHS) |
| Pseudostem appearance | Dull |
| The predominant underlying color of the pseudostem | Orange (27D, RHS) |
| Pigmentation of the underlying pseudostem | Red (51B, RHS) |
| Sap color | Watery (157D, RHS) |
| Wax-on leaf sheaths | Moderately waxy |
| Number of suckers | 3 |
| Development of suckers | >¼ and <¾ of the height of the parent plant |
| Position of suckers | Close to parent (vertical growth) |
| Blotches at the petiole base | Sparse blotching |
| Blotches color | Greyed-Brown (N199A, RHS) |
| Petiole canal leaf III | Wide with erect margins |
| Petiole margins | Winged and clasping the pseudostem |
| Wing type | Dry |
| Petiole margin color | Without color |
| Edge of petiole margin | Colourless (Without a color line along) |
| Petiole margin width | 1 to 3 cm |
| Leaf blade length | 150 to 170 cm |
| Leaf blade width | 50 to 70 cm |
| Petiole length | 40 to 50 cm |
| Color of the leaf's upper Surface | Green (137A, RHS) |
| Appearance of leaf upper surface | Dull |
| Color of the leaf's lower surface | Green (N138B, RHS) |
| The appearance of the leaf's lower surface | Dull |
| Wax on leaves | Very waxy |
| The insertion point of the leaf blade on the petiole | Symmetric |
| The shape of the leaf blade base | Both sides rounded |
| Leaf corrugation | Even, smooth |
| Color of midrib dorsal surface | Green (143B, RHS) |
| Color of midrib ventral surface | Green (136D, RHS) |
| Color of cigar leaf dorsal surface | Yellow-Green (147D, RHS) |
| Blotches on leaves of water suckers | Without blotches |
| Peduncle length | 20 to 30 cm |
| Empty nodes on the peduncle | One |
| Peduncle width | 4 to 6 cm |
| Peduncle color | Green (141B, RHS) |
| Peduncle hairiness | Very hairy, short hairs (similar to velvet touch) |
| Bunch length | 51 cm |
| Bunch diameter | 57 cm |
| Number of hands per bunch | 8 |
| Bunch position | Horizontal |
| Bunch shape | Cylindrical |

-continued

| | |
|---|---|
| Bunch appearance | Lax |
| Flowers that form the fruit | Female |
| Fruits | Biseriate |
| Rachis type | Present and male buds may be degenerated or persistent |
| Rachis position | At an angle |
| Rachis appearance | Male flowers/bracts above the male bud |
| Male bud type | Normal (present) |
| Male bud shape | Like a top |
| Male bud size | 21 to 30 cm |
| Bract base shape | Large shoulder |
| Bract apex shape | Intermediate |
| Bract imbrication | Young bracts considerably overlap. |
| Color of the bract external face | Red-Purple (59A, RHS) |
| Color of the bract internal ace | Red-Purple (59C, RHS) |
| Color of the bract apex | Tinted with yellow (discolored) (7C, RHS) |
| Color stripes on the bract | Without discolored lines (not ridges) on the external face |
| Bract scars on rachis | Very prominent |
| Persistence of the bracts of the rachis | Moderate |
| Fading of color on bract base | Color discontinuing towards the base. |
| Male bract shape | Ovate |
| Male bract lifting | Not Lifting from male bud (bracts are persistent) |
| Bract behavior before falling | Revolute (Rolling) |
| Wax on the bract | Very few waxes |
| Presence of grooves on the bract | Moderate |
| Male flower behavior | Neutral/male flowers are persistent. |
| Compound tepal basic color | Greyed-Orange (166A, RHS) |
| Compound tepal pigmentation | Rust-colored spots (79A, RHS) |
| Lobe color of compound tepal | Yellow (2B, RHS) |
| Lobe development of compound tepal | Developed |
| Free tepal color | Opaque White (155D, RHS) |
| Free tepal shape | Rectangular |
| Free tepal appearance | Simple folding under the apex |
| Free tepal apex development | Developed |
| Free tepal apex shape | Triangular |
| Anther exertion | Inserted |
| Filament color | Greyed-White (156D, RHS) |
| Anther color | Green-White (157C, RHS) |
| Pollen sac color | White-cream (1C, RHS) |
| Pollen vitality | Abundant |
| Style basic color | Green-White (157C, RHS) |
| Pigmentation on style | Without pigmentation |
| Style exertion | Inserted |
| Style shape | Curved under stigma |
| Stigma color | Greyed-Orange (167D, RHS) |
| Ovary shape | Straight |
| Ovary basic color | White (155C, RHS) |
| Ovary pigmentation | Very few or no visible signs of pigmentation |
| The dominant color of male flower | White 155C, RHS) |
| Irregular flowers | Absent |
| Arrangement of ovules | Two rowed |
| Fruit position | Perpendicular to the stalk |
| Number of fruits | 9 to 12 |
| Fruit length | 12 to 15 cm |
| Fruit width (finger) | 2.5 to 3 cm |
| Fruit shape (longitudinal curvature) | Straight in the distal part |
| Color of the flesh of the fruit | Creamy (158C, HRS) |
| Longitudinal ridges of the fruit | moderate |
| Transverse section of fruit | Rounded |
| Fruit apex | Bottle-necked |
| Remains of flower relicts at the fruit apex | Persistent style |
| Fruit pedicel length | 7 to 10 mm |
| Fruit pedicel width | 3 to 5 mm |

-continued

| | |
|---|---|
| Pedicel surface | Hairless |
| Fusion of pedicel | Very partially or no visible sign of fusion |
| Immature fruit peel color | Yellow-Green (144C, RHS) |
| Mature fruit peel color | Yellow (9B, RHS) |
| Fruit peel thickness | 1.5 to 2 mm |
| Adherence to the fruit peel | Fruit peels easily |
| Cracks in fruit peel | Without Cracks |
| Pulp in fruit | With pulp |
| Pulp color before maturity | White (155B, RHS) |
| Pulp color at maturity | Yellow-White (158A, RHS) |
| Fruits fall from hands. | Deciduous |
| Flesh texture | Soft |

-continued

| | |
|---|---|
| Predominant taste | Sweet (like Cavendish) |
| Presence of seed with the source of pollen | Without seeds |
| Seed surface | Without seeds |
| Seed shape | Without seeds |
| Growth habit of the plant | Spreading |

The invention claimed is:

1. A new and distinct variety of banana plant named 'NW02', substantially as illustrated and described herein.

* * * * *

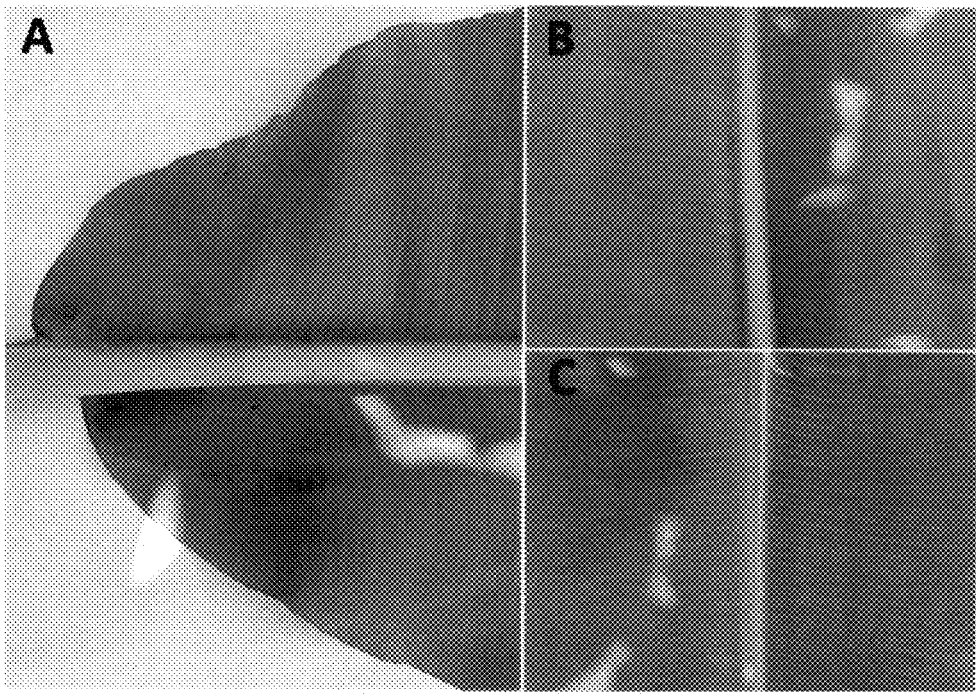
FIG. 3A, 3B, & 3C
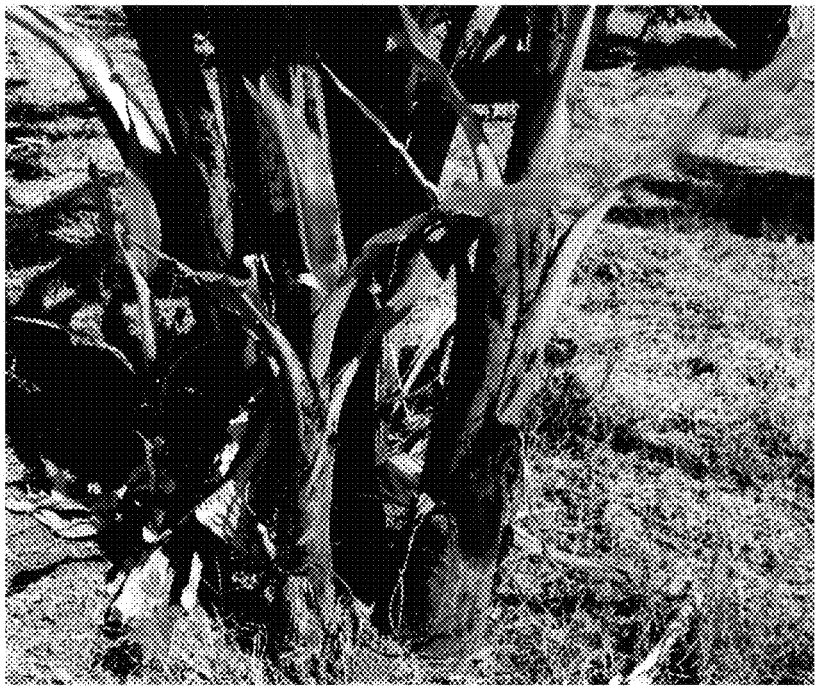
FIG. 4

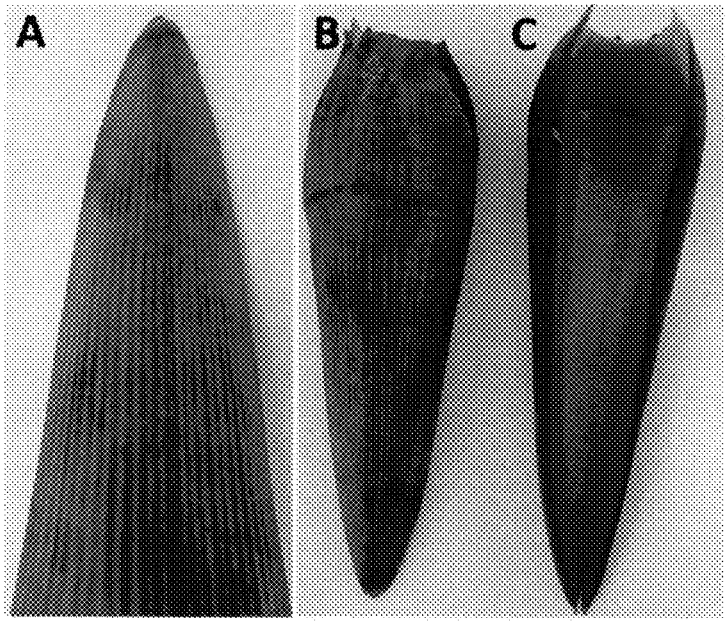
FIG. 7A, 7B, & 7C
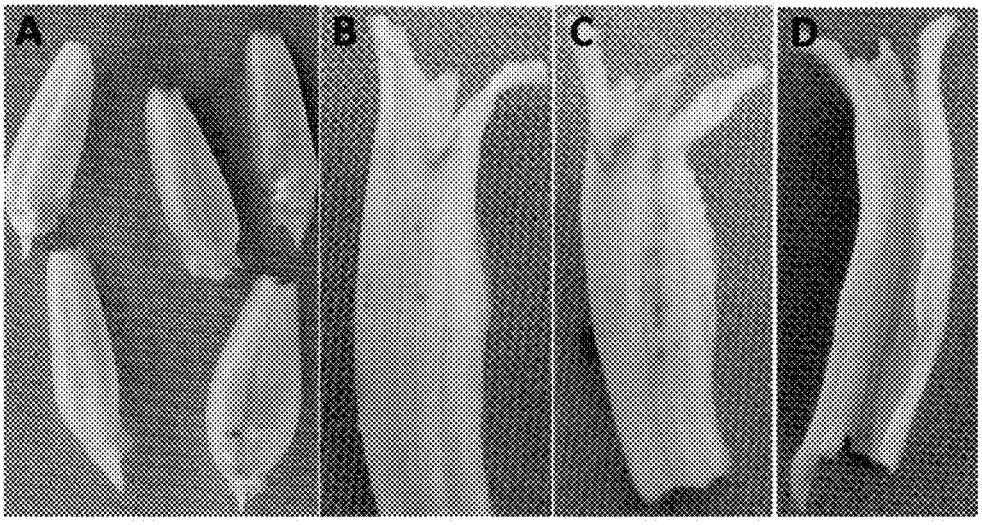
FIG. 8A, 8B, 8C, & 8D